(12) United States Patent
Pansiera (10) Patent No.: US 8,083,701 B2
(45) Date of Patent: Dec. 27, 2011

(54) MULTI-CENTRIC ORTHOPEDIC HINGE JOINT

(75) Inventor: Timothy Pansiera, Weaverville, NC (US)

(73) Assignee: OTS Corporation, Weaverville, NC (US)

( * ) Notice: Subject to any disclaimer, the term of this patent is extended or adjusted under 35 U.S.C. 154(b) by 781 days.

(21) Appl. No.: 12/214,866

(22) Filed: Jun. 23, 2008

(65) Prior Publication Data

US 2008/0319363 A1      Dec. 25, 2008

Related U.S. Application Data

(60) Provisional application No. 60/936,802, filed on Jun. 25, 2007.

(51) Int. Cl.
*A61F 5/00* (2006.01)
(52) U.S. Cl. .............................. 602/16; 602/20; 602/23
(58) Field of Classification Search .................... 602/16, 602/5, 20, 23, 26–29; 128/883
See application file for complete search history.

(56) References Cited

U.S. PATENT DOCUMENTS

| | | | |
|---|---|---|---|
| 5,328,446 A | 7/1994 | Bunnell et al. | |
| 6,027,466 A | 2/2000 | Diefenbacher et al. | |
| 6,039,709 A | 3/2000 | Bzoch | |
| 6,736,567 B1 * | 5/2004 | Dibello | 403/353 |
| 6,969,364 B2 * | 11/2005 | Sterling | 602/16 |
| 7,189,212 B2 | 3/2007 | Popp et al. | |
| 7,306,572 B2 * | 12/2007 | Ceriani et al. | 602/16 |

* cited by examiner

*Primary Examiner* — Kim Lewis
(74) *Attorney, Agent, or Firm* — Chambliss, Bahner & Stophel, PC (57) ABSTRACT

A multi-centric orthopedic joint having inner and outer guide plates and upper and lower arms rotatably connected to the guide plates for pivotal movement therebetween. The plates each include upper and lower pairs of curved bean shaped slots, tilted relative to one another. The arms include a proximal end, the proximal end further including pins positioned and proportioned for complimental sliding movement within the upper and lower slots of the guide plates. Set screws are positioned between the inner and outer guide plate against a locking surface of the proximal end of each arm. When the set screws are loosened the upper and lower arms may be moved relative to one another, permitting the guide pins to slide within the slots but in opposite directions relative to one another. Flat-screws secure the inner and outer guide plates and co-act with the set screws as a locking mechanism of proximal ends of said arms at a desired angulation between them.

7 Claims, 6 Drawing Sheets

MULTI-CENTRIC ORTHOPEDIC HINGE JOINT

CROSS REFERENCE TO RELATED APPLICATION

This application claims the benefit under 35 USC 119(e) of the provisional patent application Ser. No. 60/936,802, filed Jun. 25, 2007, which is hereby incorporated by reference in its entirety.

BACKGROUND OF THE INVENTION

1. Area of the Invention

The present invention relates generally to orthopedics and more particularly to a multi-centric hinge joint for use in knee braces.

2. Prior Art

Hinge joints that operate to support or assist injured or infirmed body limbs are known in the art. Such devices typically comprise a pair of relatively moveable support members attached respectively to different parts of the body, for example, the upper and lower leg. In addition, some form of articulation means provides a resilient or other controlled or controllable interconnection between the proximal and distal members of the support device.

It is desirable for a hinge joint to provide control of an upper limb relative to a lower limb. Further, it is desirable for hinge joints to support and assist in the effective functioning of the limb, allowing the limb to attain certain limited degrees of motion and flexibility in predetermined directions in a manner that resembles normal body movement.

U.S. Pat. No. 5,328,446 (to Bunnell et al.) teaches a joint device that includes two extending sidearms, each sidearm secured by a sleeve, cast or brace to the patient's limb so that the sidearms are on opposite sides of the afflicted joint. The joint device pivotally connects the two sidearms and includes a selectively actuated one-way clutch which allows movement in one direction while inhibiting it in the other.

U.S. Pat. No. 6,027,466 (to Diefenbacher et al.) teaches an orthopedic joint for connection between first and second body parts for movement in a flexion/extension plane between adjustable stops.

U.S. Pat. No. 6,039,709 (to Bzoch) teaches a pair of opposed exterior plates containing slots for receiving an adjustment wheel threaded to a screw positioned in close association with gear teeth juxtaposed to the second end portion of a first elongated bar. The exterior plates enclose the second end of two elongated bars. The exterior plates are locked together with rivets to hold the gear teeth in position and permit movement or locking of the second elongated bar by manipulation of the adjustment wheel.

U.S. Pat. No. 7,189,212 (to Popp et al.) teaches a hinge for orthopedic braces which includes a pair of support arms, a pair of pivot pins and a hinge plate. The arms are coupled to the hinge plate through the pivot pins and are rotatable between an extension position and a flexion position. The hinge plate has a plurality of adjustment apertures for selective reception of an extension limit pin and a flexion limit pin to selectively restrain rotation of the arms beyond an extension limit and a flexion limit. The pins are retained on the hinge by flexible retainers and are individually positioned among the apertures to adjust the range of motion of the arms.

Hinge joints for knee braces in the prior art are bulky, heavy and difficult to adjust. They may make use of a wheel with gear teeth, a pawl and ratchet or other means that may fail to provide a user with the smooth sliding action of an uninjured knee.

Thus, there remains a need for a hinge joint that will provide versatility of motion that is simple, adjustable and unobtrusive and operates in a manner that mimics the anatomical motion of a knee.

SUMMARY OF THE INVENTION

The present invention relates to is a multi-centric orthopedic joint having upper and lower arms. The upper and lower arms each have a proximal end and a distal end, with the proximal end of each arm including a locking surface. Further, there is provided an outer guide plate and an inner guide plate. The outer and inner guide plates each include two pairs of curvilinear bean shaped slots. The slots on the outer guide plate are mirror images of the slots on the inner guide plate. In addition, the slots of the slot pairs on the guiding plates are tilted relative to the other, so that within each pair of slots, the concave region of one slot faces the concave region of the other, but at an angle between the major axes of the respective slots. The extent of the major axis of each slot establishes its range of motion.

The proximal end of each arm includes guide pins. In a preferred embodiment, a pair of guide pins are positioned at the proximal end of each arm. The guide pins project outwardly in the direction of the outer guide plate with the opposite ends of the pins projecting toward the inner plate. The slots are proportioned for receiving the guide pins. Set screws, such as Allen screws are positioned between the inner and outer guide plate against the locking surface of the proximal end of each arm. When the set screws are loosened the upper and lower arms may be moved relative to one another, permitting the guide pins to slide in opposite directions relative to one another. Thus, an angle of rotation is effected by the movement of the upper and lower arms relative to one another, allowing a complete range of motion that mimics the rotation of an anatomical knee joint. Adjustment of the set screws establishes the range of rotation of the pins within the curved slots. tabs. Flat slot head screws secure the inner and outer guide plates to one another and may be adjusted to control the friction of rotation of the members relative to the guide plates. Said slot screws also co-act with the set screws as a locking mechanism.

It is a principal object of the present invention to provide an orthopedic joint with a range of rotation defined by the shape, length and relative angulation of said curved slots.

Another object is to afford an orthopedic joint that does not utilize a wheel with gear teeth, or a pawl and ratchet mechanism, to achieve a desired angle of rotation. Herein, the motion of each group of outer and inner guide pins, relative to the guide plates, enables rotation between the upper and lower arms of the joint, thereby achieving a range of motion and planetary gear action of a smooth sliding nature resembling normal motion of the body.

A further object of the invention is to provide an orthopedic joint having versatility and range of motion that is adjustable at many positions.

Another object is to provide an orthopedic joint that is simple, light weight and unobtrusive.

A further object of the invention is to provide an orthopedic joint that is adaptable to a highly compact size for infant and pediatric, as well as adult use.

The above and yet further objects and advantages of the present invention will become apparent from the hereinafter set forth Detailed Description of the Invention, the Drawings, and the Claims appended herewith.

BRIEF DESCRIPTION OF THE DRAWINGS

The present invention may be better understood by reference to the following detailed description taken in conjunction with the accompanying drawings, wherein.

DETAILED DESCRIPTION OF THE INVENTION

The present multi-centric orthopedic joint may be seen to include an upper arm 10, a lower arm 12, an outer guide plate 34, an inner guide plate 36, transverse plate X or slot screws 44 and 46, and Allen head set screws 48 and 50.

With respect to details of said upper and lower arms, and outer and inner guide plates, upper arm 10 may be seen to include a proximal end 14 and a distal end 18, the proximal end also including a locking surface 30. Projecting axially outward in the direction of outer plate 34 are upper guide pins 22 and 24. Opposite axial ends of said pins, that is, pins 22.1 and 24.1 of the upper arm project toward inner plate 36. Similarly, proximal end 16 includes its locking surface 32 of lower member 12 and integral axial pins 26 and 28 which project outwardly, while mirror images thereof project axially in the direction of inner guide plate 36.

As may be seen with reference to the views of FIGS. 2-8, each of said pin sets 22/22.1 and 24/24.1, upon assembly, insert into curvilinear bean-shaped slot 23 as to pin 22.1, and slot 23.1 as to pin 22. Similarly, pin 24 is proportioned for insertion into slot 25.1 while pin 24.1 is proportioned for insertion into slot 25. The same arrangement is employed with respect to the lower arm 12. In particular, pin 26 inserts into curved slot 27.1 of plate 34; pin 26.1 inserts into curved slot 27 of plate 36, pin 28 inserts into curved slot 29.1; and pin 28.1 inserts into curved slot 29 of inner plate 36. The assembly of all of these pieces, inclusive of transverse screws 44 and 46 and set screw 48 and 50 are further shown in the views which follow.

Figure 1:
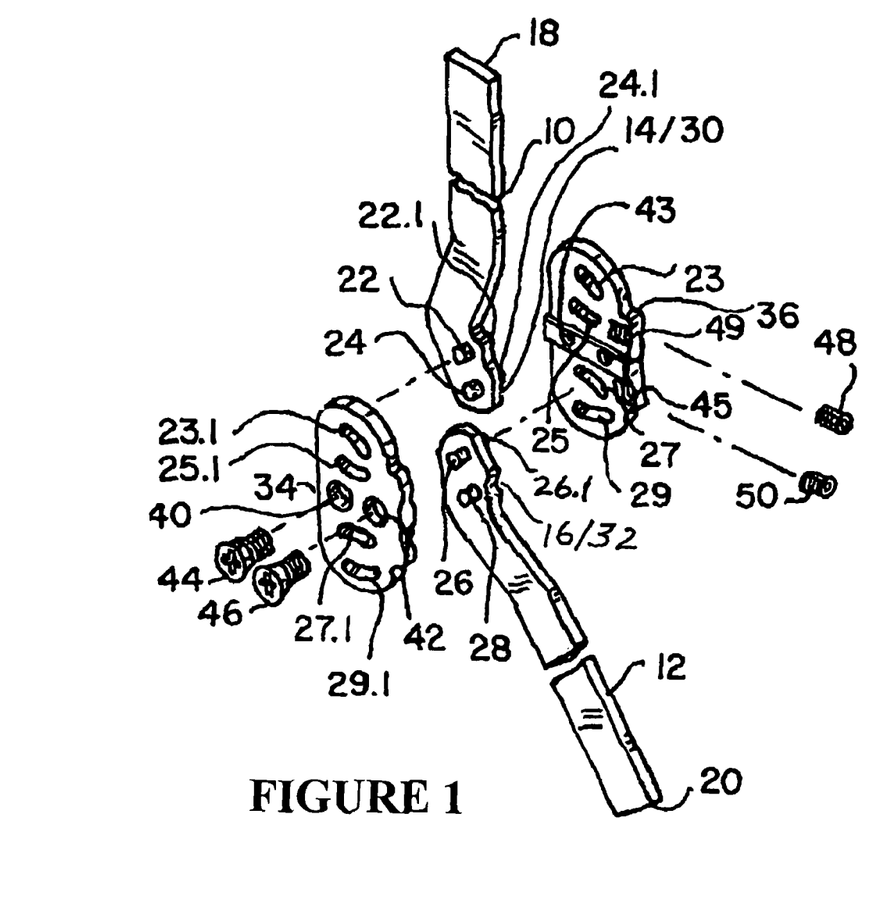
FIG. 1 is an exploded plan view of the various elements of the multi-centric hinge orthopedic joint of the present invention.
Figure 2:
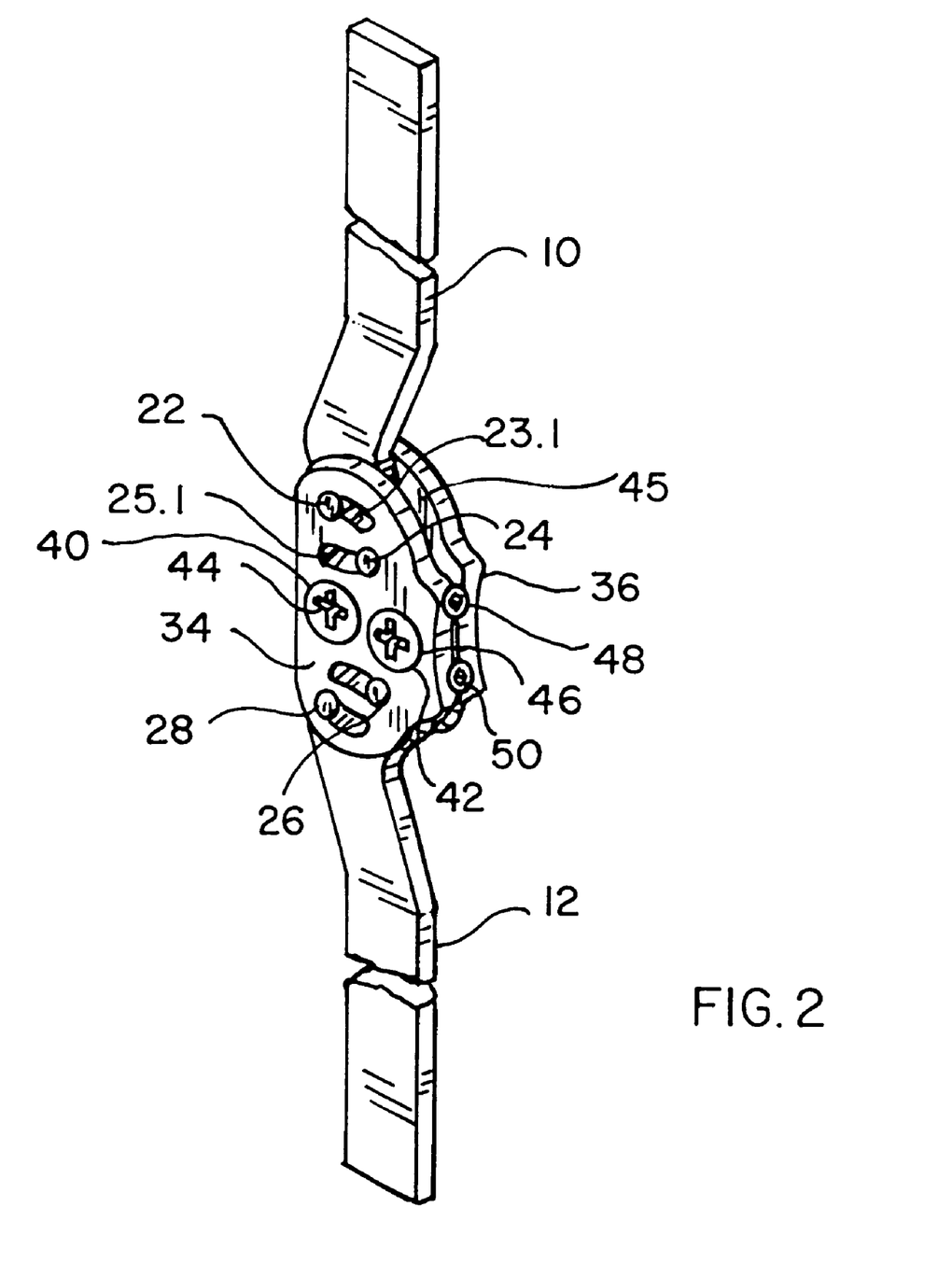
FIG. 2 is a side perspective view of the assembled multi-centric hinge orthopedic joint.
Figure 3:
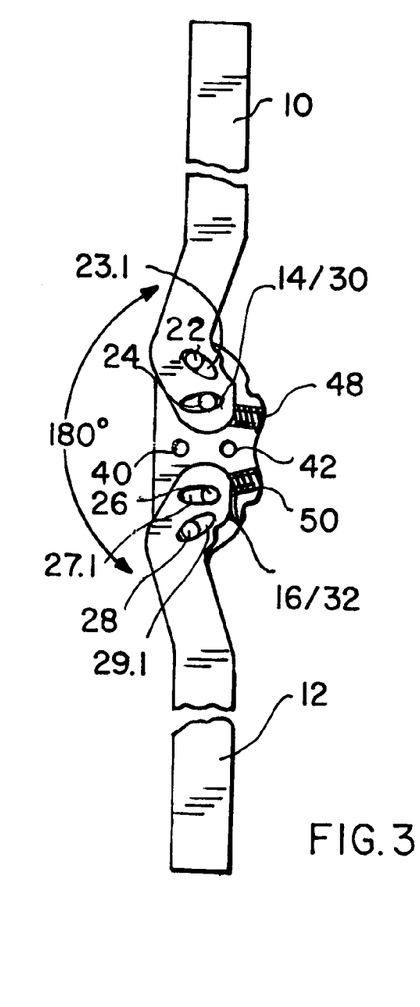
FIG. 3 is a reverse opposite side perspective view, relative to FIG. 2, of the assembled multi-centric hinge orthopedic joint of the present invention in a state of extension about a rotational axis showing a 180 degree angle between the upper and lower arms.

More particularly, in FIG. 2 flat head slot screws 44 and 46 pass within apertures 40 and 42 of front plate 34 as well as the corresponding receiving apertures 43 and 45 of back plate 36 (see FIG. 1). Also, set screws 46 and 50 are shown secured between the respective plates 34 and 36 in their condition of fullest possible advance against respective locking surface 30, of upper member 18, and 32 of lower member 12, thereby producing an approximately 180 degree relationship between said upper and lower members 10 and 2, in the brace position shown in FIGS. 2 and 3.

Figure 4:
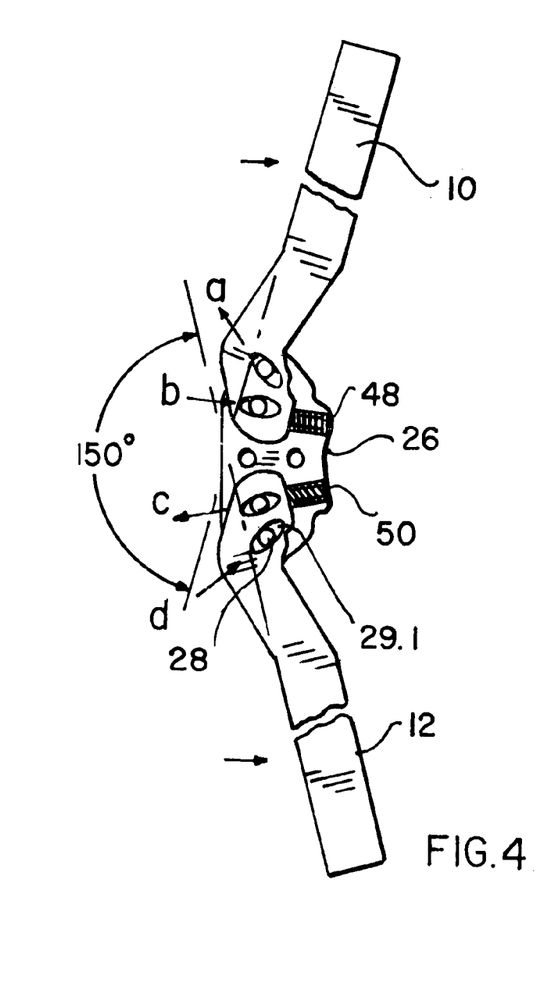
FIG. 4 is a side perspective view similar to that of FIG. 3 of the assembled multi-centric hinge orthopedic joint in a state of flexion about a rotational axis showing (a) a 150 degree angle between the upper and lower arms, and (b) relative direction of movement of the pins of the hinge during flexion.
Figure 5:
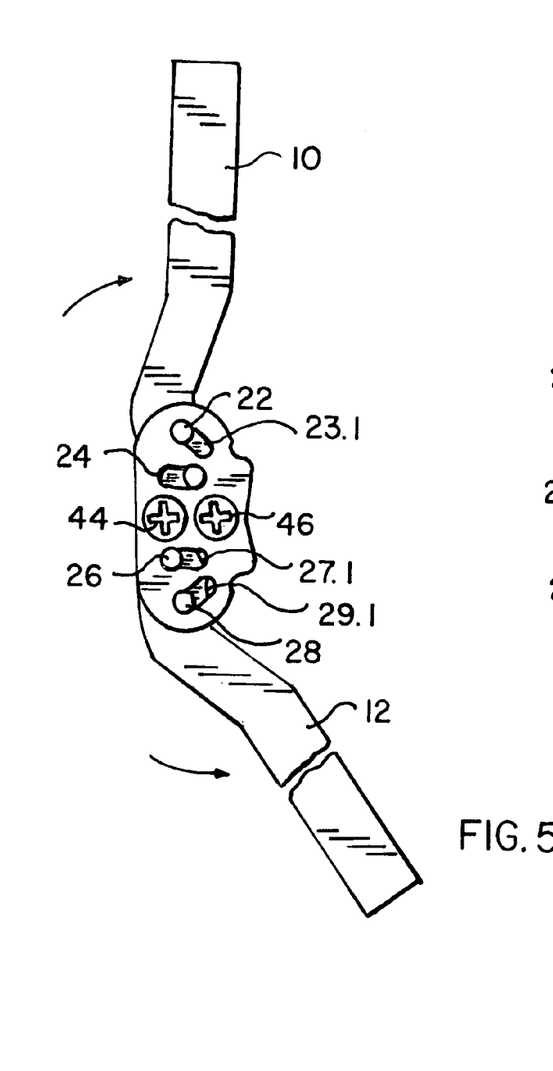
FIG. 5 is a perspective view in the direction of FIG. 2 of the multi-centric hinge orthopedic joint of the invention in a state of flexion and is a reverse view of the view of FIG. 4.
Figure 6:
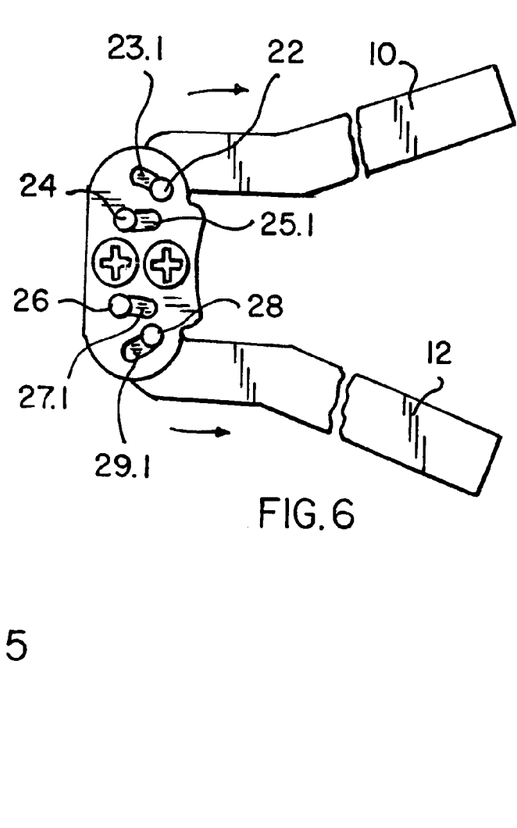
FIG. 6 is a perspective view in the direction of FIG. 6 of the multi-centric hinge orthopedic joint showing the upper and lower arms in a state of maximum flexion, that is, at an angle of about thirty degrees each relative to the axis of the x-screws.
Figure 7:
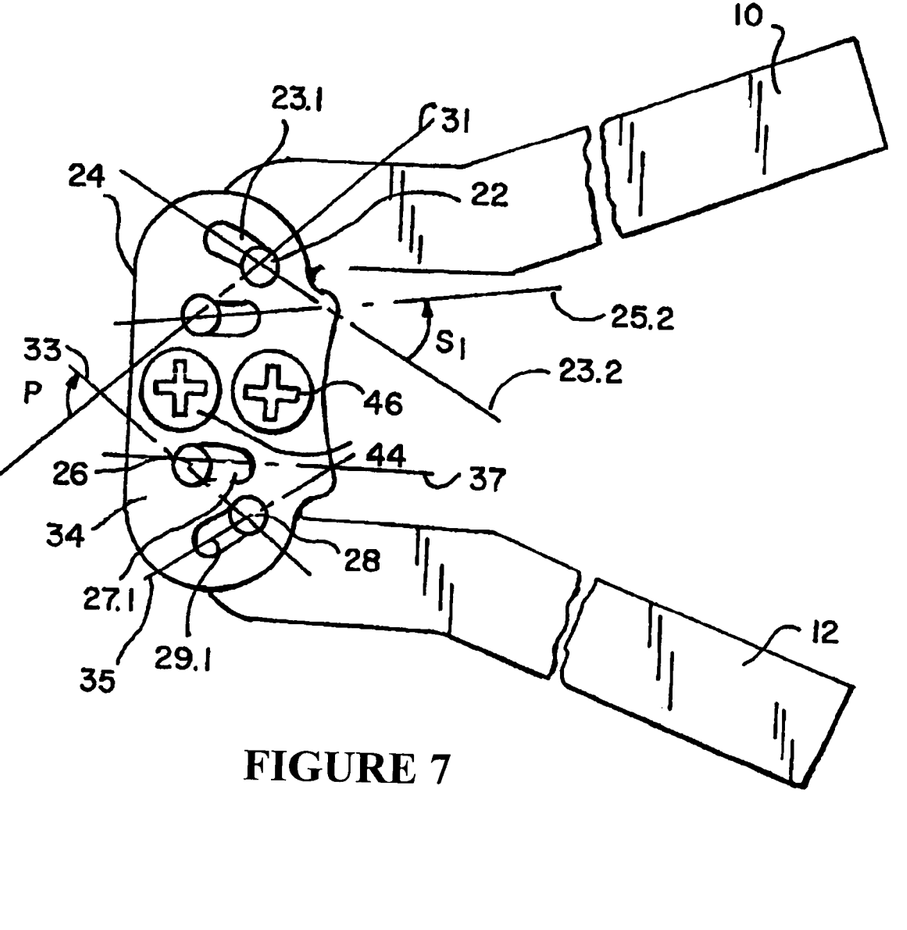
FIG. 7 is a plan side and enlarged view of FIG. 6 of the multi-centric hinge orthopedic joint showing the upper and lower arms in a state of maximum flexion and illustrating the movement of the upper and lower guide pins within the respective curvilinear bean shaped slots relative to one other about an axis of rotation.

To change the angular relationship between arms 10 and 12 from that of greatest extension, shown in FIG. 4, the set screws 48 and 50 are backed-off to permit pin pairs 22/24, and 26/28 to arc in opposite directions a/b and c/d respectively (see small opposing arrows in center of FIG. 4) within their respective curved slots 23.1, 24, 25.1, 27.1 and 29.1 respectively. From FIG. 7, one may see the rotation of arm 10 by the extent of angle S1, the same being the case with respect to lower arm 12 when the pins 26 and 28 thereof are rotated into a position away from that of FIGS. 2 and 3. Intermediate arm positions are shown in FIGS. 4 and 5, FIG. 4 showing a 150° angle between the respective arms 10 and 12. A further angular variable is dictated by the radian of polar rotation of up to about 30° defined by each of the slots 23.1, 25.1, 27.1 and 29.1, reflected in the angle P which is defined by the intersection of respective pin axes 31 and 33 shown in the closure position in FIG. 7. Other variables in the invention which affect the extent of rotation of upper arm 10 relative to lower arm 12, are said angle S1 at the intersection of the axes 23.2 and 25.2 of slots 23.1/25.1 (see FIG. 7) and the extent of axial advance of the set screws within channels 45 and 49 (see FIG. 1) against the respective locking surfaces 30 and 32 of members 10 and 12. It is accordingly to be appreciated that several variables influence and affect the extent of angulation or rotation of the upper arm relative to the lower arm of the brace, thus allowing a complete range of motion thereof.

Figure 8:
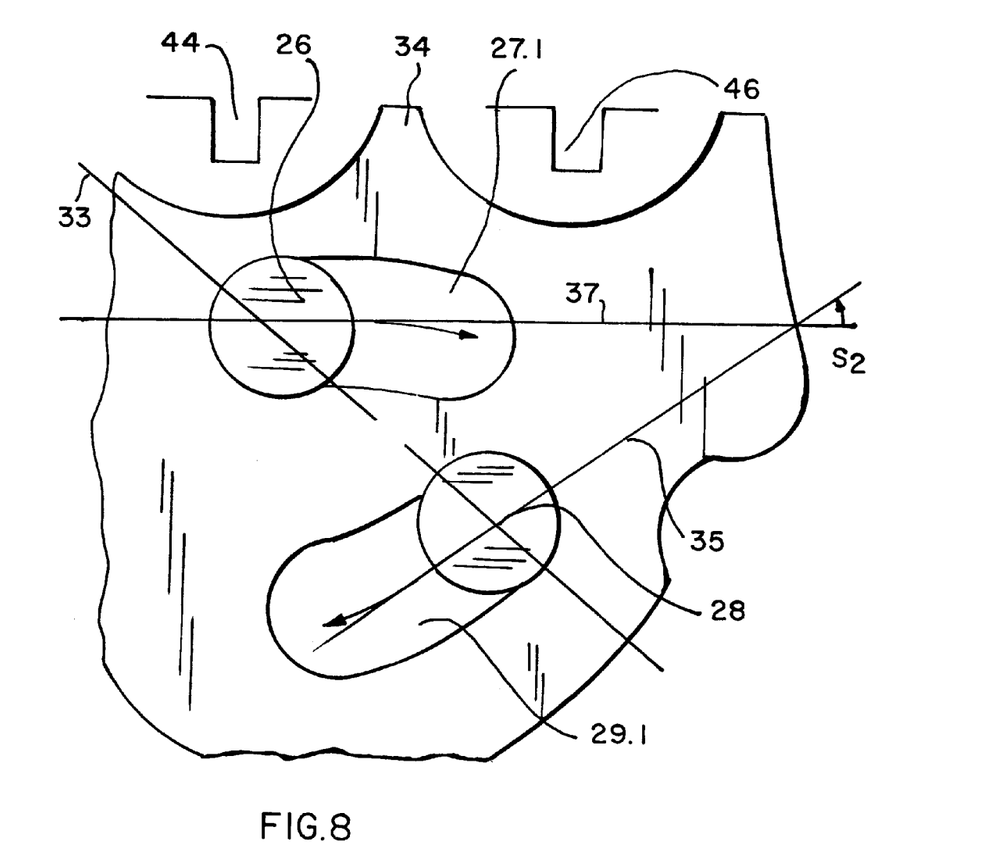
FIG. 8 is an enlarged view of the lower left portion of FIG. 7.

An enlargement of the lower left portion of front plate 34 is shown in FIG. 8. Therein may be seen the curved or bean-like shape of the slots 27.1 and 29.1 respectively. It is in part, the slightly curved nature of the axes of slots 27.1 and 29.1 which facilitates the smooth rotational movement of the pins 26 and 28 from the position shown in FIG. 3 to that shown in FIGS. 4/5/6. It may be further appreciated that the center of rotation of lower arm 12 occurs at a point midway between pins 26 and 28 as indicated by the X symbol on axis 33 therebetween in FIG. 8. In other words, pins 26 and 28 rotate in the fashion of a planetary gear, about an imaginary center of rotation X therebetween. The nature or rotation between upper and lower legs 10 and 12 is further influenced by the angle between slot axes 35 and 37, indicated by angle S2 in FIGS. 7 and 8. These factors assure a sliding arc-like motion of the pins in the slots that mimics the anatomical sliding action of the knee. In a given application, angle S1 need not equal angle S2.

The above system is adaptable to a highly compact size for infant and pediatric, as well as adult use. Also, anatomical knee hyperextension is controlled by the use of stops, namely, said set screws 48/50. The system results in cumulative range of adjustment shown in FIGS. 3-6. Slot screws 44 and 46 also co-act with the set screws 48 and 50 as a locking mechanism of said arms 10 and 12 relative to each other.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as claimed herewith.

What is claimed is:

1. A multi-centric hinge orthopedic joint for use in limb braces to provide control of an upper limb relative to a lower limb, comprising:
    (a) an outer guide plate in which the outer guide plate includes two slot sets, each of upper and a lower curved slots, each set comprising slots of substantially equal length, each slot titled relative to the other in which a closest region therebetween exists at a posterior part of said plate and a farthest distance therebetween exists at an anterior part of said plate;
    (b) an inner guide plate, substantially a mirror image of said outer guide plate, in which said inner guide plate further includes two sets of upper and a lower curved slots, each set comprising slots of substantially like geometry to said slots of said outer plate, each slot of each set titled relative to the other in which a closest region therebetween exists at a posterior part of said plate and a farthest distance therebetween exists at an anterior part of said plate;
    (c) means for complementally connecting said outer guide plate to said inner guide plate;
    (d) an upper arm, including a distal and a proximal end, said proximal end of said arm further including a locking surface, said surface positioned between said inner and outer guide plates, for pivotal movement therebetween;
    (e) a lower arm, including a distal and proximal end, said proximal end of said arm further including a locking surface, said locking surface positioned between said inner and outer guide plates for pivotal movement therebetween; and
    (f) means for providing selectable pressure against said locking surfaces of said upper and lower arms to define a desired position of one relative to the other.

2. The multi-centric hinge of claim 1, in which said means for providing selectable pressure comprises Allen head set screws.

3. The multi-centric hinge of claim 1, in which a locking means comprising flat slot head screws passing through said inner and outer plates is provided.

4. The multi-centric hinge of claim 1, in which said proximal end of each of said upper and lower arms each include integral transverse pins, positioned and proportioned for complemental sliding motion within said slots.

5. The multi-centric hinge of claim 1, in which said proximal end of each of said upper and lower arms each include a pair of integral pins, positioned and proportioned for complemental sliding motion within said upper and lower slot sets of the outer and inner guide plates.

6. The multi-centric hinge of claim 5, in which each slot set defines a mirror image of the slot set of each plate when viewed along a plane of rotation of said upper and lower arms relative to each other.

7. The multi-centric hinge of claim 5, in which said upper and lower arms rotate about an axis, at a point substantially medially between said pairs of pins.

* * * * *

UNITED STATES PATENT AND TRADEMARK OFFICE
CERTIFICATE OF CORRECTION

| | | |
|---|---|---|
| PATENT NO. | : 8,083,701 B2 | Page 1 of 1 |
| APPLICATION NO. | : 12/214866 | |
| DATED | : December 27, 2011 | |
| INVENTOR(S) | : Timothy Pansiera | |

It is certified that error appears in the above-identified patent and that said Letters Patent is hereby corrected as shown below:

At column 5, line 13 delete "titled" and substitute therefor --tilted--

At column 5, line 22 delete "titled" and substitute therefor --tilted--

Signed and Sealed this
Sixth Day of March, 2012

David J. Kappos
*Director of the United States Patent and Trademark Office*